US00PP14114P29

(12) United States Plant Patent
Lemon

(10) Patent No.: US PP14,114 P2
(45) Date of Patent: Aug. 26, 2003

(54) GERANIUM PLANT NAMED 'CANDY CARDINAL'

(75) Inventor: David Lemon, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/245,060

(22) Filed: Sep. 17, 2002

(51) Int. Cl.[7] ..... A01H 5/00
(52) U.S. Cl. ..... Plt./330
(58) Field of Search ..... Plt./330

*Primary Examiner*—Kent Bell
(74) *Attorney, Agent, or Firm*—Webb Ziesenheim Logsdon Orkin & Hanson, P.C.

(57) ABSTRACT

A new and distinct early flowering zonal geranium plant with deep red colored flowers above dark green foliage and having excellent outdoor heat tolerance.

1 Drawing Sheet

Botanical classification: *Pelargonium×hortorum* (zonal geranium).

Varietal denomination: 'Candy Cardinal'.

BACKGROUND OF THE INVENTION

The present invention comprises a new and distinct cultivar of *Pelargonium×hortorum* known by the varietal name 'Candy Cardinal'. The new variety was discovered in a selected breeding program in Lompoc, Calif. as Breeder No. 5DG2259-1. The new variety is a result of cross breeding of an unnamed, unpatented plant (breeder no. 1263, female) and 'Sassy Dark Red' (male, U.S. Plant Pat. No. 8,053). The new variety exhibits similar flower color to the male parent and similar dark leaf color to the female parent. The new variety differs from its parents in that the female parent has a more bluish flower color and the male parent has a lighter green foliage color. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 8 weeks from a rooted cutting to flowering in a 6 inch pot. The response time was determined on plants grown in soilless media employing constant fertilizer 200–250 parts per million of nitrogen and potassium in full light.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. Plants were about 12 weeks old when described. The color readings were taken on a plant under 65–85 foot candles of fluorescent cool white light. Color references are primarily to The R.H.S. Colour Chart of The Royal Horticultural Society of London.

PLANT

Form: Medium mound; free basal branching.
Height: 13 cm from media surface to top of foliage in a 16 inch pot.
Diameter: 24 cm.
Strength: Does not require artificial support.
Rooting time: Roots visible to outside of a dirt plug in 10–14 days.
Leaves:
- *Arrangement.*—Alternate.
- *Stipules.*—Two per node.
- *Size.*—Length: 4–6.2 cm. Width: 5.5–7 cm. Zone: 1.7 cm from petiole attachment; zone is 7 mm wide.
- *Shape.*—Reniform; cordate base, rounded apex.
- *Margin.*—Crenate.
- *Texture.*—Velvety with pubescence.
- *Color.*—Upper surface: 137A. Lower surface: 137C. Zone: 139A.
- *Ribs and veins.*—Venation: Palmate. Color: 144A.

Petioles:
- *Color.*—137C with anthocyanin staining of 187A.
- *Length.*—4–5.2 cm.

Stem:
- *Color.*—144A with anthocyanin staining of 187A.
- *Length.*—17 cm.
- *Internode length.*—1–2.5 cm.

THE BUD

Shape when no color showing:
- *Overall.*—Elliptical cluster.
- *Individual bud.*—Elliptical or oval.

Size when no color showing:
- *Overall.*—2–2.5 cm across cluster.
- *Individual bud.*—6–8 mm long; 4–6 mm wide.
- *Color (just prior to sepals parting at tips).*—45B.

Number of buds per cluster: 20–25.

INFLORESCENCE

Blooming habit: Continuous flowering throughout growing season, free and early blooming.
Size of umbel: 10–13 cm in diameter, 7 cm in depth.

Borne: Umbel, flowers on pedicel, pedicel on peduncle, 7–10 cm above foliage.

Flowers:

*Form.*—Flat to slightly cupped.

*Number of flowers per umbel.*—17–23.

*Size.*—Diameter: 4.5–5.5 cm. Depth: 0–2 cm.

Petals:

*Color.*—Upper surface: From the outer edges to the middle, 45B fades to 61C, then near the base fades to 40A. In the top 2–3 petals near the base, 40A fades to 40C. Also in the top 2–3 petals, there is venation of 185B. Lower surface: The edges begin with 45C and fade to 43C. Towards the base 43C fades to 63C then to white, 155D. Venation shows through from the upper surface. Shape: Inverted teardrop; pointed base, rounded apex. Size: 2.5–3 cm long; 1.9–2.4 cm wide. Margin: Entire. Number per flower: 8–10. Texture and appearance: Velvety, smooth, highly reflective.

Tonality from a distance: Deep red showy flowers that stand out atop the dark green mound of foliage.

Petaloids:

*Quantity.*—2–7. Shape: Irregular; some twisted; tubular. Color: Same as petals.

Sepals:

*Quantity.*—5.

*Shape.*—Narrow; nearly parallel at base, narrows to point; pointed apex, entire margin.

*Size.*—0.9–1.1 cm long; 0.2–0.4 cm wide.

*Color.*—Upper and lower surface: 144B with 187B at base.

Pedicel:

*Length.*—2.8–3.7 cm.

*Color.*—144B with heavy anthocyanin staining, 187B, starting near the point of flower attachment and fading to lighter staining of 185B where the pedicel meets the peduncle.

Peduncle:

*Length.*—10–14 cm.

*Color.*—144B with anthocyanin staining of 187B.

Lasting quality: Umbels last 7–14 days; individual flowers last 6 days.

Disease/pest resistance: No susceptibility to diseases or pests has been noted to date.

REPRODUCTIVE ORGANS

Stamens:

*Anthers.*—2–3 mm in length.

*Filaments.*—Length: 6–7 mm. Color: White. Pollen: Orange.

Pistils:

*Number.*—One.

*Length.*—1.1–1.3 cm.

*Stigma.*—Number: One. Color: Red.

*Style.*—Length: 4–5 mm. Color: Red.

*Ovaries.*—Superior, mildly pubescent, 4–5 mm long, 1.8–2.1 mm wide, purple.

Fruit: None observed.

I claim:

1. A new and distinct variety of geranium plant substantially as shown and described.

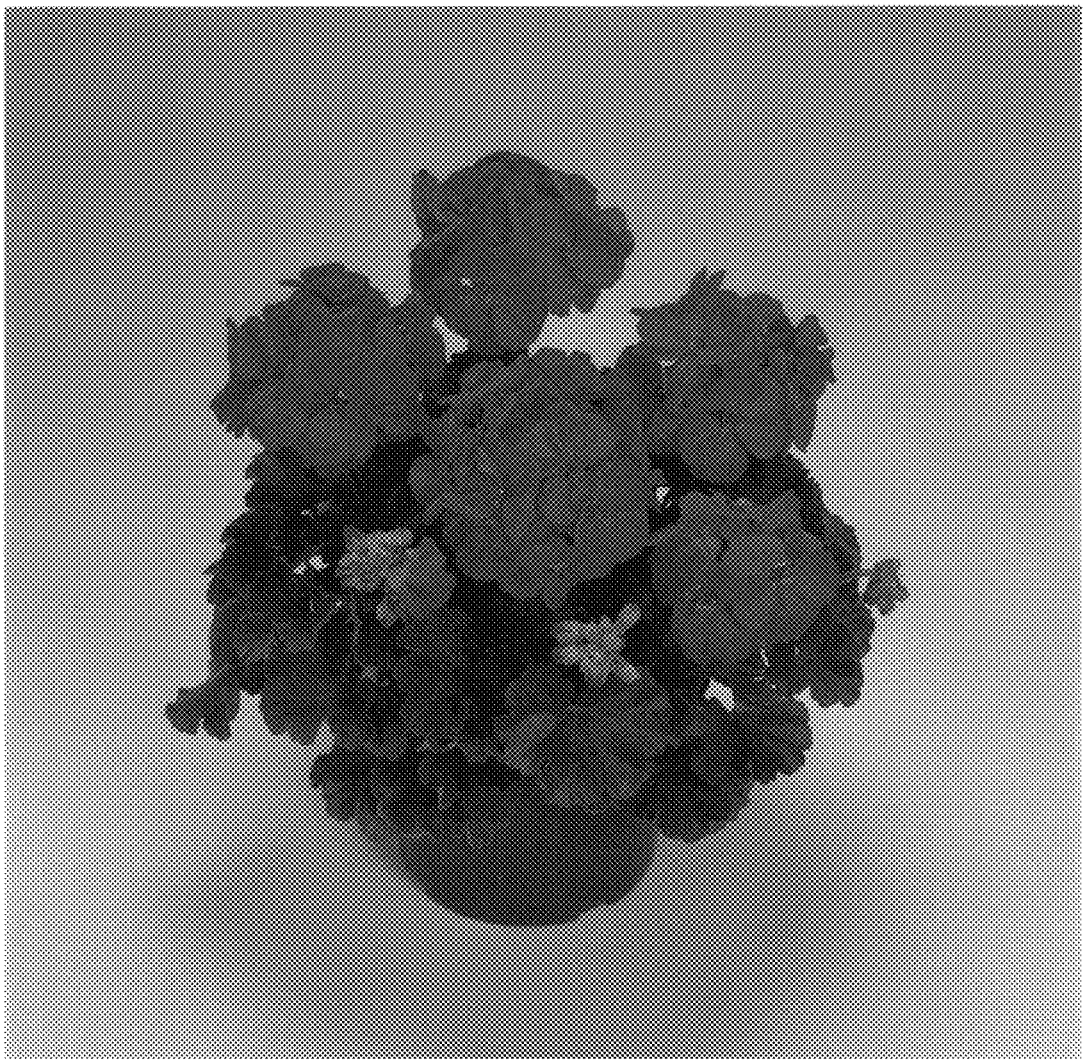

* * * * *